US006256859B1

(12) United States Patent
Stoddard et al.

(10) Patent No.: US 6,256,859 B1
(45) Date of Patent: Jul. 10, 2001

(54) METHOD OF MANUFACTURING AN ASPIRING TOOL

(75) Inventors: Robert Stoddard, Steamboat Springs; Arlan James Reschke, Longmont, both of CO (US)

(73) Assignee: Sherwood Services AG, Schaffhausen (CH)

( * ) Notice: Subject to any disclaimer, the term of this patent is extended or adjusted under 35 U.S.C. 154(b) by 0 days.

(21) Appl. No.: 09/298,125

(22) Filed: Apr. 23, 1999

Related U.S. Application Data

(60) Provisional application No. 60/101,703, filed on Sep. 25, 1998.
(51) Int. Cl.[7] .............................. B21B 1/46; B21B 13/22; B22D 11/126; B22D 11/128; B23P 17/00
(52) U.S. Cl. ............................ 29/527.4; 604/22; 29/558
(58) Field of Search .................................. 29/558, 527.4; 408/1 R; 604/22

(56) References Cited

U.S. PATENT DOCUMENTS

| D. 388,170 | 12/1997 | Sjostrom . | |
|---|---|---|---|
| 4,406,284 | 9/1983 | Banko . | |
| 4,425,115 | 1/1984 | Wuchinich . | |
| 4,526,571 | 7/1985 | Wuchinich . | |
| 4,531,934 | 7/1985 | Kossovsky et al. . | |
| 4,816,018 | 3/1989 | Parisi . | |
| 4,869,715 | * | 9/1989 | Sherburne ........................... 604/22 |
| 4,923,441 | * | 5/1990 | Shuler ................................. 604/22 |
| 5,061,238 | * | 10/1991 | Shuler ................................. 604/22 |
| 5,151,084 | * | 9/1992 | Khek ................................... 604/22 |
| 5,222,937 | 6/1993 | Kagawa . | |
| 5,269,297 | 12/1993 | Weng et al. . | |
| 5,304,115 | 4/1994 | Pflueger et al. . | |
| 5,318,570 | 6/1994 | Hood et al. . | |
| 5,324,297 | 6/1994 | Hood et al. . | |
| 5,346,469 | 9/1994 | Ikeda et al. . | |
| 5,359,996 | 11/1994 | Hood . | |
| 5,382,228 | 1/1995 | Nita et al. . | |
| 5,413,556 | 5/1995 | Whittingham . | |
| 5,417,672 | 5/1995 | Nita et al. . | |
| 5,433,702 | 7/1995 | Zelman et al. . | |
| 5,464,389 | 11/1995 | Stahl . | |
| 5,527,273 | 6/1996 | Manna et al. . | |
| 5,562,609 | 10/1996 | Brumbach . | |
| 5,562,610 | 10/1996 | Brumbach . | |
| 5,688,235 | 11/1997 | Sakurai et al. . | |
| 5,718,676 | * | 2/1998 | Barrett ................................ 604/22 |

* cited by examiner

*Primary Examiner*—S. Thomas Hughes
*Assistant Examiner*—Jermie E. Cozart

(57) ABSTRACT

An ultrasonic surgical apparatus for fragmenting and aspirating tissue is disclosed. The apparatus includes a handpiece which encloses a transducer, an aspirating tool, and a connector body connecting the aspirating tool and the transducer. The aspirating tool includes a elongated boy having a centrally located throughbore, a hexagon engagement portion, a threaded proximal end and a distal tip. Methods of manufacturing aspirating tools having small and large diameter throughbores adapted for use with a common handpiece are also disclosed.

15 Claims, 7 Drawing Sheets

METHOD OF MANUFACTURING AN ASPIRING TOOL

This application claims benefit to U.S. provisional application 60/101,703 filed Sep. 25, 1998.

BACKGROUND

1. Technical Field

The present disclosure relates to ultrasonic surgical apparatus for fragmenting and aspirating tissue. More specifically, the present disclosure relates to aspirating tools suitable for use in an ultrasonic surgical apparatus for aspirating tissue and to a method of manufacturing such aspirating tools.

2. Background of Related Art

Devices which effectively utilize ultrasonic energy for a variety of applications are well-known in a number of diverse arts. The application of ultrasonically vibrating surgical devices used to fragment and aspirate unwanted tissue with significant precision and safety has led to the development of a number of valuable surgical procedures. Accordingly, the use of ultrasonic aspirators for the fragmentation and surgical removal of tissue from a body has become known. Initially, the technique of surgical aspiration was applied for the fragmentation and removal of cataract tissue. Later, such techniques were applied with significant success to neurosurgery and other surgical specialties where the application of ultrasonic technology through a handheld device for selectively removing tissue on a layer-by-layer basis with precise control has proven feasible.

Typically, ultrasonic surgical devices for fragmenting and aspirating tissue include an ultrasonic transducer supported within a handpiece, an ultrasonically vibrating tool, an extender connecting the tool to the ultrasonic transducer and a sleeve or flue positioned about the tool. The tool includes a longitudinally extending central bore having one end located adjacent a distal tip and a second end located adjacent the proximal end of the tool. The proximal end of the tool is adapted to engage a vacuum source to facilitate aspiration of fluid. The flue is positioned about the tool to define an annular passage. Irrigation fluid is supplied through the annular passage around the tip to the surgical site where it mixes with blood and tissue particles and is aspirated through the bore in the tool. By mixing the irrigation fluid with the blood and tissue particles, coagulation of the blood is slowed down and aspiration thereof is aided. U.S. Pat. Nos. 5,015,227 and 4,988,334 disclose such ultrasonic surgical devices and are hereby incorporated by reference.

In any surgical procedure, it is necessary that a surgeon be afforded good visibility of the surgical site. Thus, it is important that the ultrasonic tool and flue be configured and dimensioned not to obscure visibility at the surgical site. One problem associated with manufacturing small diameter tools for the above-described ultrasonic surgical devices is machining an even smaller throughbore in the tool. Presently, tools with throughbores having diameters as small as 0.062 inches are known. Efforts to consistently manufacture ultrasonic tools having smaller diameter throughbores have not proven feasible.

Ultrasonic tools having large diameter throughbores are also advantageous during certain surgical procedures. For example, where highly compliant tissue mixed with blood is aspirated, there is increased likelihood of occlusion of the aspiration conduit due to the coagulation of the blood. To make matters worse, ultrasonic vibration of the tool acts to increase the rate of coagulation of the blood within the tool.

One problem associated with manufacturing ultrasonic tools having large diameter throughbores is that the threaded connector on the tool must be dimensioned to be attached to the same handpiece to which the small diameter tools are to be attached. Therefore, in large diameter tools, there is less material between the base of the threads on the threaded connector at the proximal end of the tool and the throughbore. As a result, the fracture rate of the large diameter ultrasonic tools is substantially higher than that of small diameter ultrasonic tools in the area of the threads.

Accordingly, a need exists for improved ultrasonic tools for use with apparatus for ultrasonically fragmenting and aspirating tissue and improved methods of manufacturing such ultrasonic tools which are more resistant to stress fracture and which have smaller diameter throughbores.

SUMMARY

In accordance with the present disclosure, an ultrasonic surgical apparatus is disclosed for fragmenting and aspirating tissue. The apparatus includes a handpiece which encloses a transducer having a magnetostrictive or piezoelectric stack. An aspirating tool having a throughbore is connected to the transducer by a connector body. A manifold having an irrigation port is positioned about the aspirating tool. During a surgical procedure, irrigation fluid is supplied through the irrigation port into manifold to the distal end of the aspirating tool, where the irrigation fluid mixes with fragmented tissue and blood from the surgical site. The blood and tissue are removed from the surgical site via the throughbore in the aspirating tool.

The handpiece is adapted to receive a plurality of different size aspirating tools. One such aspirating tool includes a throughbore having a diameter of about 0.045 inches. In order to form such a small diameter throughbore, a two-step drilling process is used. During the first step a proximal portion of the throughbore is drilled using a drill bit having a diameter of 1.25–2.5 times the desired bore diameter. During the second step, a distal portion of the bore is drilled to the desired diameter. The transition between the proximal and distal portions of the throughbore is positioned at a node.

Another aspirating tool adapted for use with the handpiece includes a throughbore having a diameter of preferably about 0.104 inches. During manufacturing, the aspirating tool is machined, the throughbore is drilled, and the proximal end of the tool is threaded. Next, the threads are masked and the aspirating tool is titanium nitride coated. By masking the threads prior to titanium nitride coating, stress concentrations formed in the threads are eliminated.

BRIEF DESCRIPTION OF THE DRAWINGS

Various preferred embodiments are described herein with reference to the drawings, wherein.

DETAILED DESCRIPTION OF PREFERRED EMBODIMENTS

Figure 1:
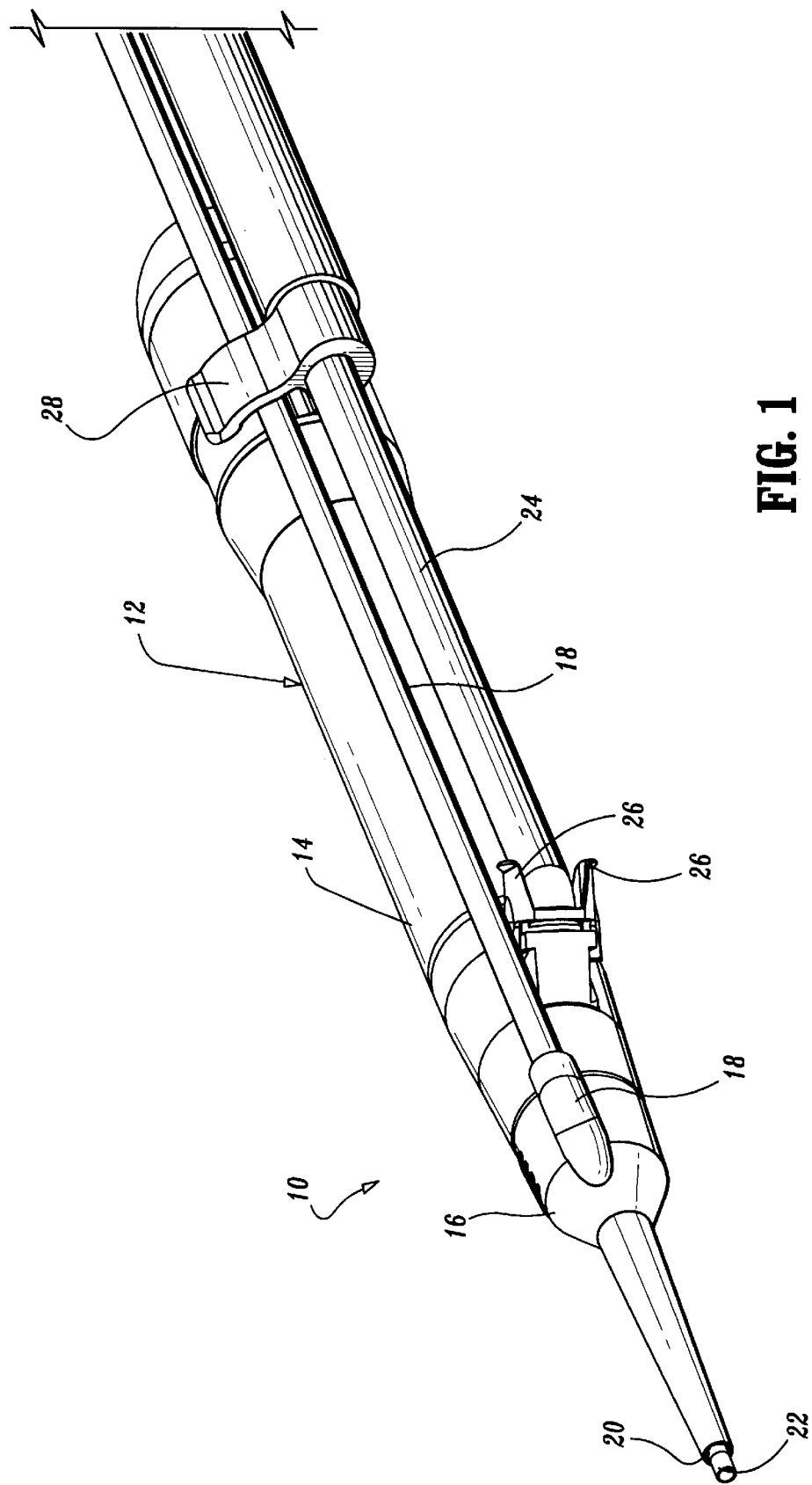
FIG. 1 is a perspective view of an ultrasonic surgical apparatus constructed in accordance with the present disclosure.

Preferred embodiments of the presently disclosed apparatus for ultrasonically fragmenting and aspirating tissue will be described in detail with reference to the drawings, in which like reference numerals designate identical or corresponding elements in each of the several views.

Figure 2:
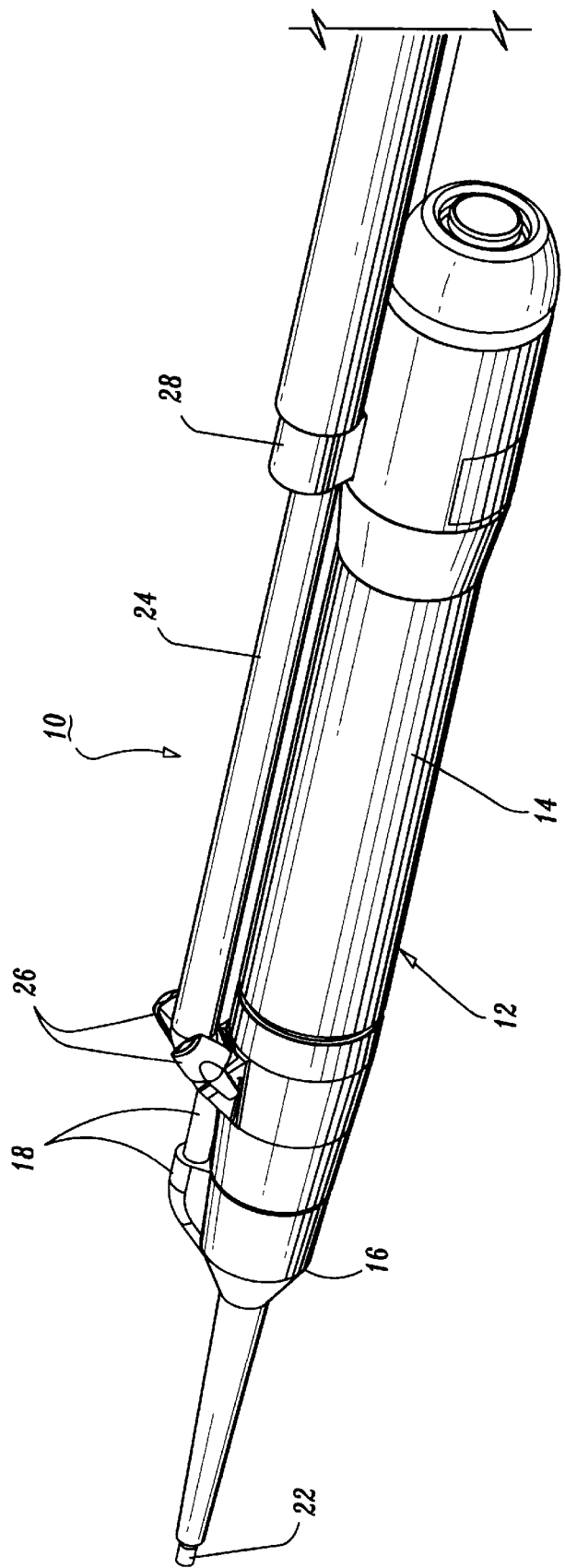
FIG. 2 is another perspective view of the ultrasonic surgical apparatus of FIG. 1 in accordance with the present disclosure.

Referring now to FIGS. 1 and 2, one embodiment of the presently disclosed apparatus for ultrasonically fragmenting and aspirating tissue is shown generally as 10. Apparatus 10 is embodied in a handpiece 12. Handpiece 12 includes a housing 14 which may be formed of a sterilizable plastic or metal, but is preferably plastic. Housing 14 connects to an irrigation manifold 16 at a distal end portion. Manifold 16 includes an irrigation port and tube 18 therein communicating with an opening 20 at a distal end thereof. A tip 22 is shown at a distal end of handpiece 12. Tip 22 is vibrated to fragment tissue during surgery as will be described in further detail hereinbelow.

An aspiration line 24 is mounted externally of housing 14. Aspiration line 24 includes release tabs 26 for dismounting a distal end portion of aspiration line 24. Further, a clip 28 is included on a proximal end portion of aspiration line 24 for holding irrigation tube 18. Tab 26 permits detachment of aspiration line 24 from housing 14 when depressed. Clip 28 permits detachment from housing 14.

Figure 3:
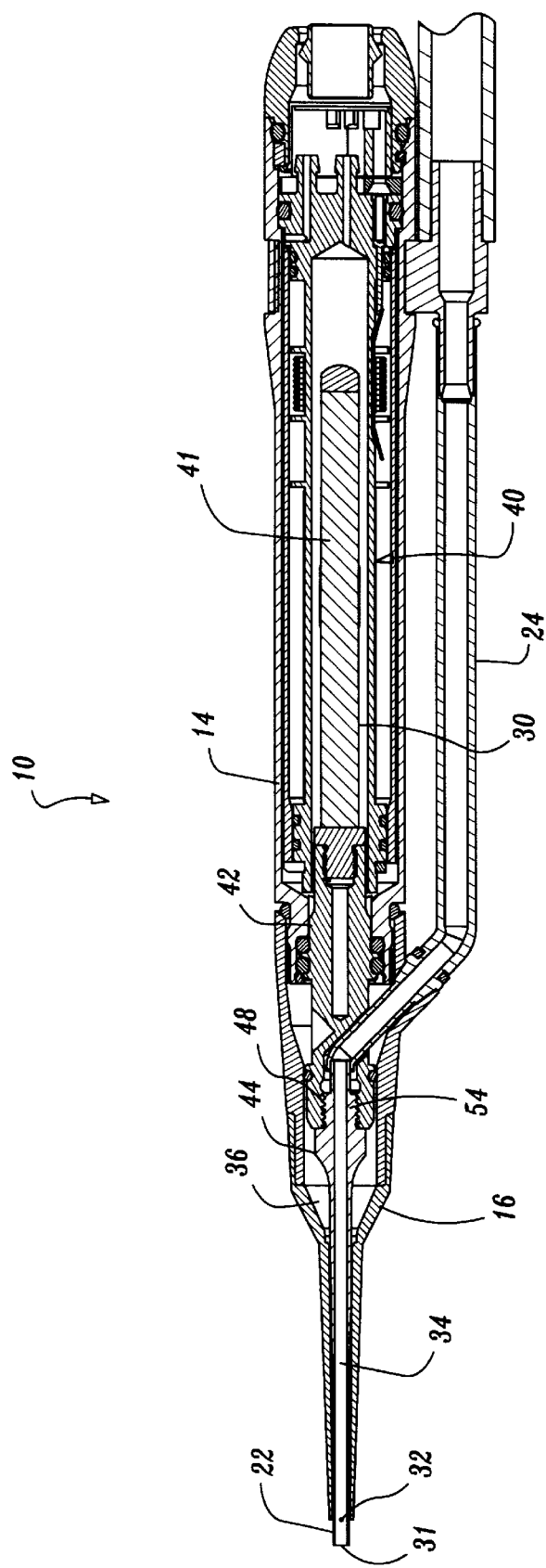
FIG. 3 is a side cross-sectional view of the surgical apparatus of FIG. 1.
Figure 4:
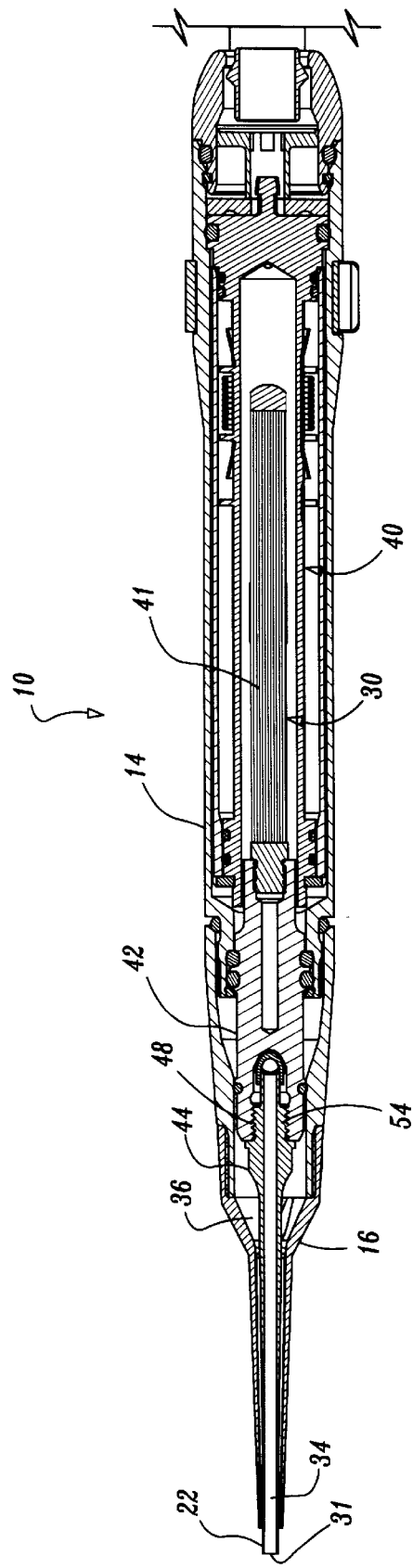
FIG. 4 is a top cross-sectional view of the surgical apparatus of FIG. 1.

Referring to FIGS. 3 and 4, housing 14 encloses a transducer housing (coilform) 40 having a magnetostrictive stack 41. An aspirating tool 44 is connected to a connecting body 42. Stack 41, connecting body 42 and tool 44 form a resonant vibrator 30 which vibrates in the ultrasonic frequency range.

Aspirating tool 44 includes a tip 22 and a throughbore 34. Tip 22 vibrates in the ultrasonic frequency range with a longitudinal amplitude in excess of about 5 mils (0.005 inch). During operation of apparatus 10, irrigation fluid is supplied through irrigation port 18 (FIG. 2) into flue 16. Flue 16 and tool 44 define an annular cavity 36 therebetween. Irrigation fluid is supplied from flue 16 through cavity 36 to the distal end of tip 22. The irrigation fluid is drawn from preaspiration holes (32) and the surgical site into inlet 31 of throughbore 34 along with fragmented tissue, blood, etc., and is removed from the surgical site via throughbore 34 and aspiration line 24. A transverse bore (preaspiration holes) 32 which communicates with throughbore 34 is formed in the distal end of tip 22. Bore 32 provides an alternate route for fluid to enter throughbore 34 when inlet 31 of aspirating tool 44 becomes clogged.

Connector body 42 includes a threaded bore 48 configured and dimensioned to receive the threaded proximal end 54 of aspirating tool 44. Although apparatus 10 is illustrated with an aspirating tool having a large diameter throughbore, different size aspirating tools, two of which will be disclosed in detail hereinbelow, can be substituted for the one presently shown. Each of the different size tools includes an identically sized threaded proximal end dimensioned to be received in threaded bore 48 of connector body 42. Thus, a variety of aspirating tools can be releasably connected to a single handpiece.

Figure 5:
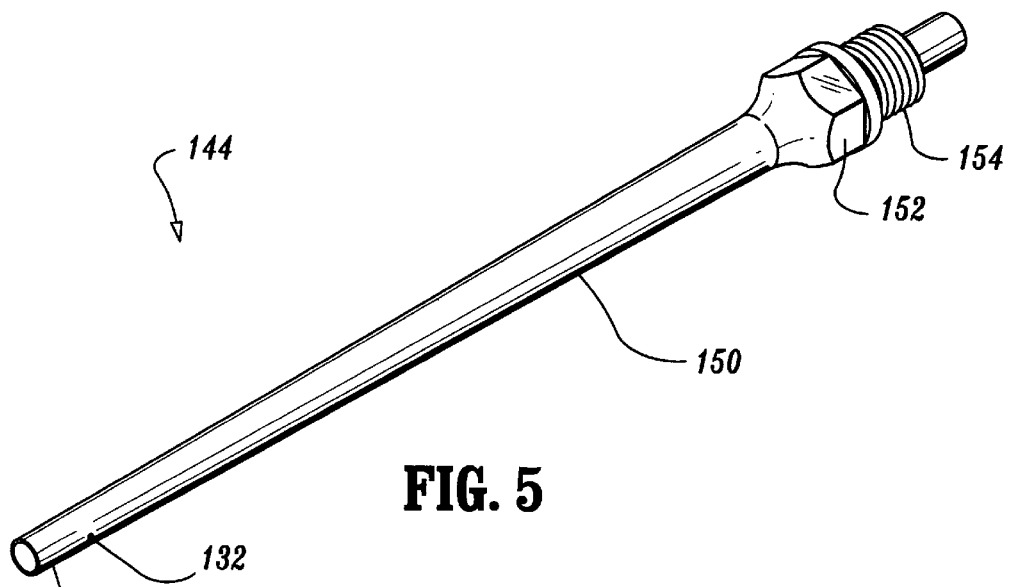
FIG. 5 is a perspective view of one embodiment of an aspirating tool suitable for use with the ultrasonic surgical apparatus shown in FIG. 1.
Figure 6:
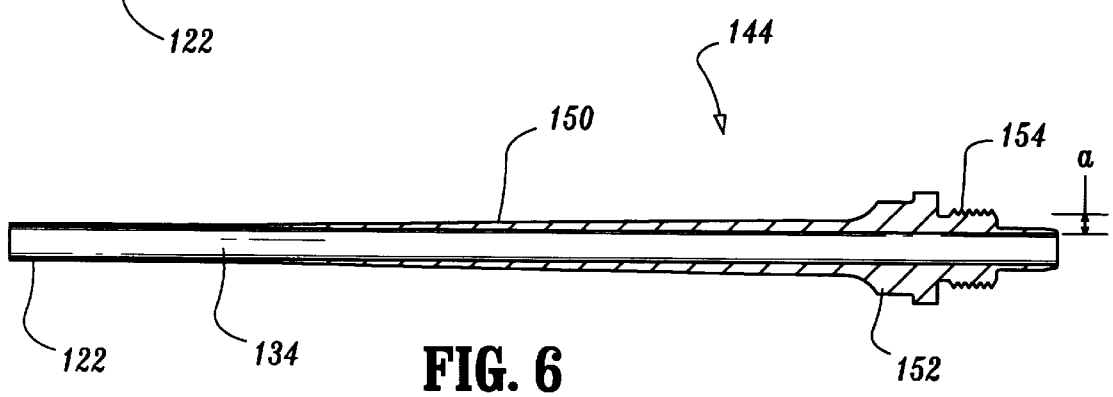
FIG. 6 is a side cross-sectional view of the aspirating tool shown in FIG. 5.
Figure 7:
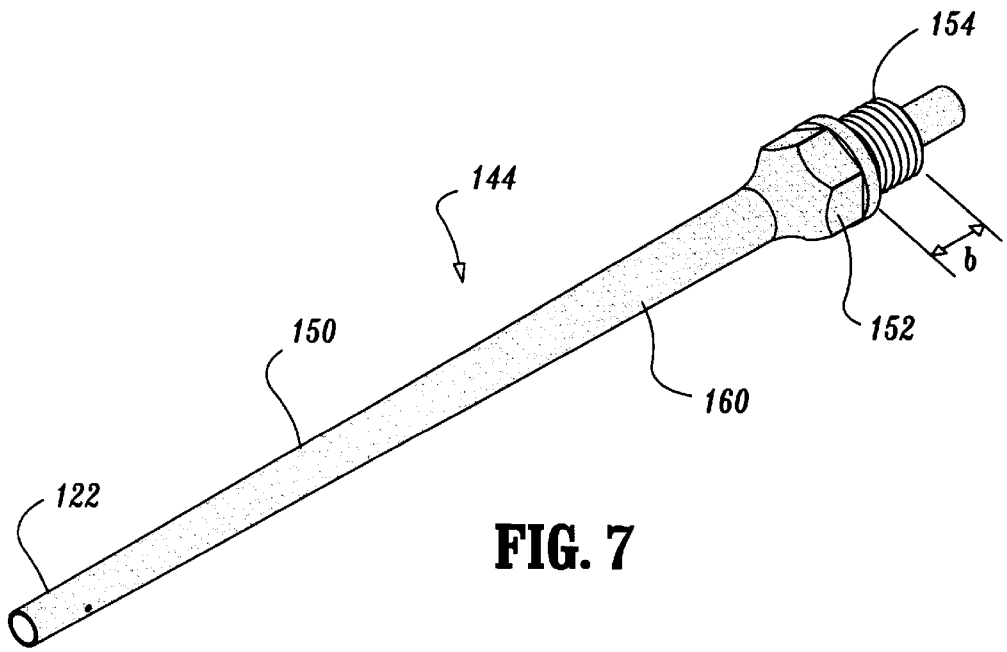
FIG. 7 is a perspective view of the aspirating tool shown in FIG. 5 with a titanium nitride coating covering all but the threads of the tool.

FIGS. 5–7 illustrate one aspirating tool 144 suitable for use with the above-described apparatus for ultrasonically fragmenting and aspirating tissue. Aspirating tool 144 includes tip 122, a large diameter throughbore 134, a transverse bore 132 communicating with throughbore 134, an elongated body 150, a hexagon engagement portion 152 and a threaded proximal end 154. Aspirating tool 144 is constructed from high-strength materials capable of handling the stress associated with ultrasonic vibration. Metals such as titanium and its alloys are preferred. Moreover, elongated body 150 is gausian to reduce the stresses to which the tool is subjected.

Referring to FIG. 6, because aspirating tool 144 includes a large diameter throughbore, which is preferably about 0.104 inches in diameter, and because threaded proximal end 154 of tool 144 has an outer diameter which is dimensioned to be received in threaded bore 48 of connector body 42 (FIG. 4), only a small amount of material, illustrated as "a" in FIG. 6, separates the base of the threads and throughbore 134. This area of reduced thickness defines a weakened portion of the aspirating tool 144 where fractures generally occur during use.

Typically, during manufacturing of an aspirating tool, after the body has been machined, the throughbore has been drilled, and the proximal end has been threaded, the entire tool is coated with titanium nitride to improve the wear resistance of the tool. Titanium nitride is brittle and has a tendency to crack. It has been discovered that when the titanium nitride cracks, stress concentrations build at the cracks. When these cracks occur on the threaded proximal end of tool 144, the thin walled material at the thread line tends to fracture. Thus, an improved method of manufacturing a large diameter bore aspirating tool has been developed. After aspirating tool 144 has been machined, throughbore 134 has been drilled, and proximal end 154 has been threaded, the threads are masked using known masking techniques. The titanium nitride coating 160 is then applied to aspirating tool 144 such that threaded proximal end 154 is not coated (See FIG. 7). By masking threaded end 154 of aspirating tool 144, illustrated as "b" in FIG. 7 during the step of titanium nitride coating, cracks resulting in stress concentrations are not formed in the threads and the aspirating tool 144 is more resistant to fracture.

Figures 8, 9:
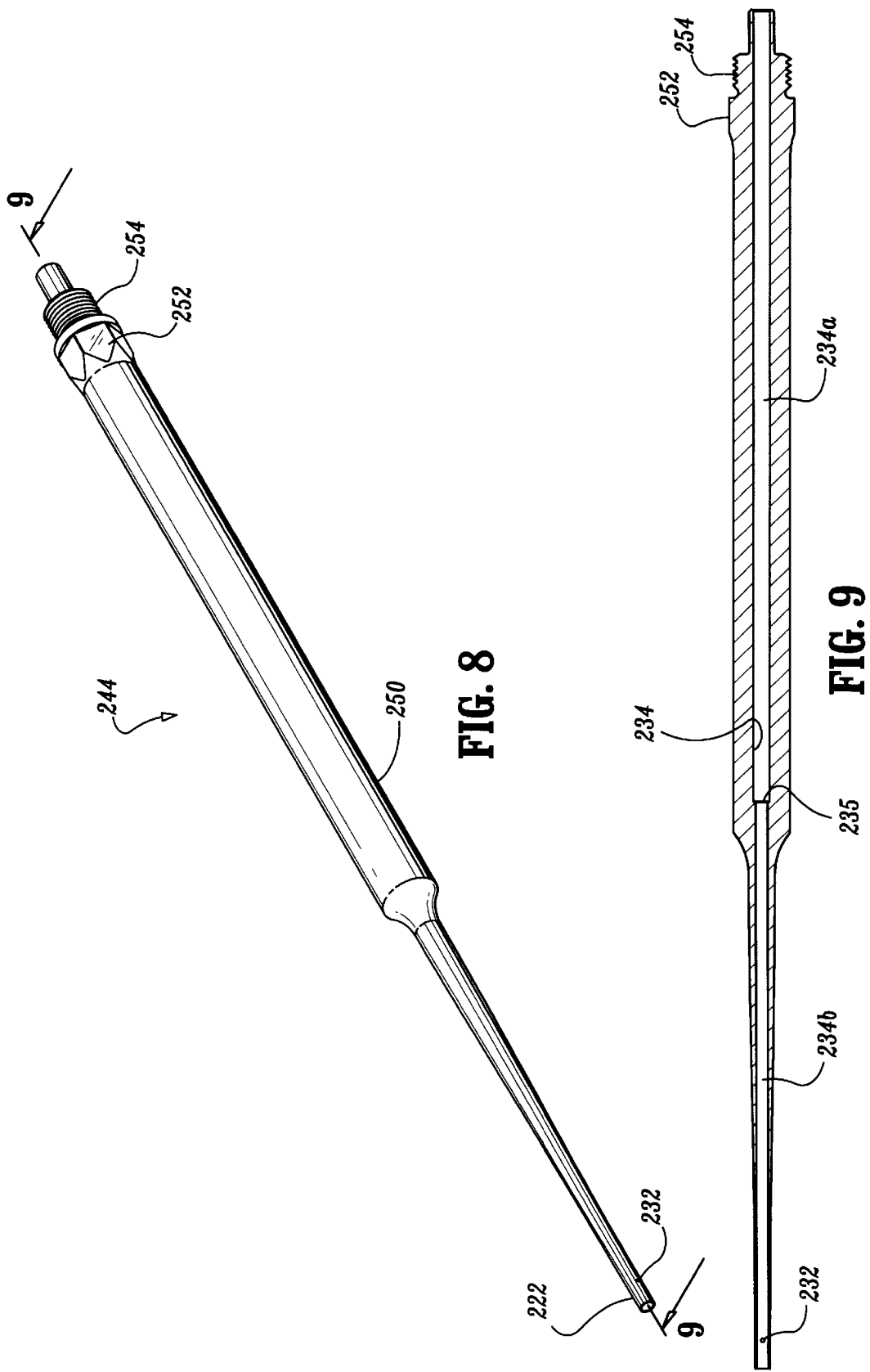
FIG. 8 is a perspective view of another embodiment of an aspirating tool suitable for use with the ultrasonic surgical apparatus shown in FIG. 1.
FIG. 9 is a side cross-sectional view of the aspirating tool shown in FIG. 8.

FIGS. 8 and 9 illustrate a small diameter aspirating tool, shown generally as 244, suitable for use with the above-described apparatus for fragmenting and aspirating tissue. Aspirating tool 244 includes an elongated body 250 having a tip 222 and a threaded proximal end 254, a stepped throughbore 234, a transverse bore 232, and a hexagon engagement portion 252. Stepped throughbore 234 includes a larger diameter proximal portion 234a and a smaller diameter distal portion 234b. Smaller diameter portion 234b is preferably about 0.045 inches in diameter.

During manufacturing of aspirating tool 244, tool body 250 is machined. Next, throughbore 234 is drilled out using a two step process. During the first step, the proximal portion 234a of throughbore 234 is drilled out using a drill bit having a diameter of about 1.25–2.5 times larger than the desired diameter of throughbore 234b. During the second step, the distal portion 234b of throughbore 234 is drilled out to the desired diameter. The transition or shoulder 235 is positioned at a node. Preferably, distal portion 234 has a diameter of about 0.045 inches. After throughbore 234 has been drilled out, proximal end 254 of aspirating tool 244 can be tapped or threaded and tool 244 can be coated with a titanium nitride coating.

Figure 10:
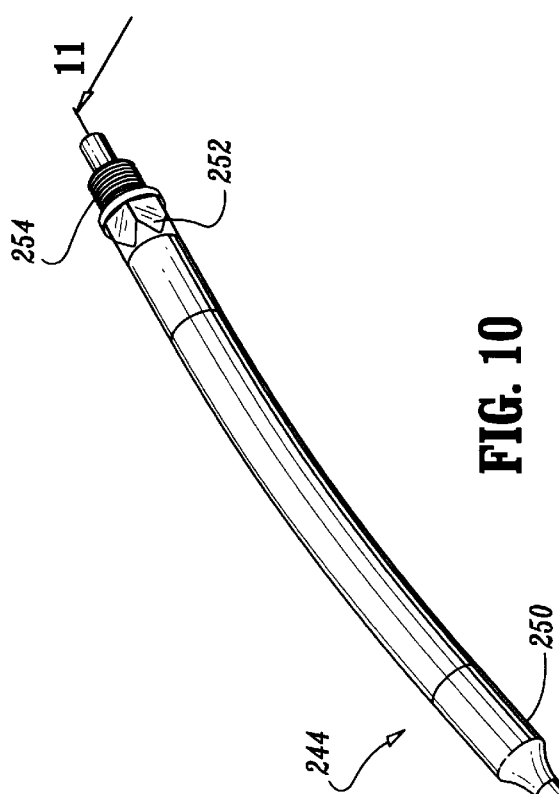
FIG. 10 is a perspective view of the aspirating tool shown in FIG. 8 after the tool has been bent.
Figure 11:
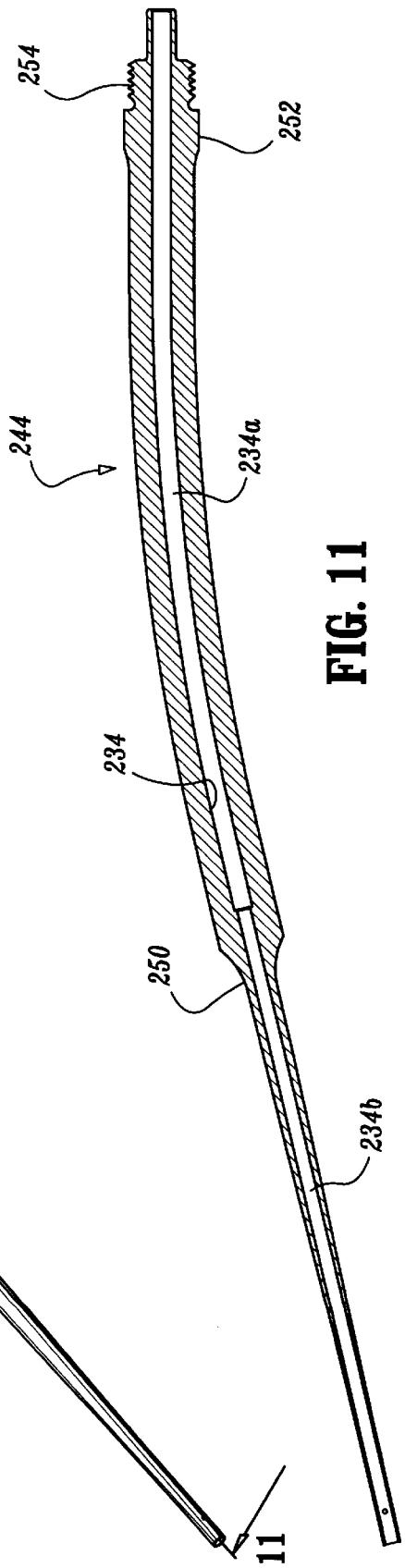
FIG. 11 is a side cross-sectional view of the aspirating tool shown in FIG. 10.

Referring to FIGS. 10 and 11, if an angled tool is desired, aspirating tool 244 can be bent after drilling throughbore 234 by inserting a metal rod (not shown) into throughbore 234 and mechanically bending aspirating tool 244 until the desired curvature is achieved. The metal rod prevents throughbore 234 from collapsing during the bending step.

It will be understood that various modifications may be made to the embodiments disclosed herein. For example, the order of the process steps for manufacturing the aspirating tools may be varied. Further, a variety of different size throughbores may be formed in the aspirating tools. Therefore, the above description should not be construed as limiting, but merely as exemplifications of preferred embodiments. Those skilled in the art will envision other modifications within the scope and spirit of the claims appended hereto.

What is claimed is:

1. A method of manufacturing an aspirating tool for use with an apparatus for ultrasonically fragmenting and aspirating tissue, comprising the steps of:
   a. machining a piece of metal stock to form a tool body including an enlarged proximal portion and an elongated distal probe portion extending from the proximal portion, the probe portion defining a longitudinal axis and having a cross-sectional dimension transverse to the longitudinal axis which decreases in the distal direction from a proximal end of the probe portion to a distal end of the probe portion;
   b. drilling a first bore having a first diameter at least partially through the enlarged proximal portion of the tool body;
   c. drilling a second bore having a second diameter smaller than the first diameter at least partially through the probe portion and communicating with the first bore; and
   d. forming a transverse bore adjacent to the distal end of the probe portion, wherein the transverse bore intersects the second bore.

2. A method according to claim 1, wherein the step of drilling the second bore includes forming the second bore having a diameter of 0.045 inches.

3. A method according to claim 1, wherein the metal stock includes titanium.

4. A method according to claim 1, wherein the step of machining a piece of metal stock includes forming screw threads on the enlarged proximal portion of the tool body.

5. A method according to claim 4, wherein the step of machining a piece of metal stock includes forming a hexagon engagement portion adjacent the enlarged proximal portion of the tool body.

6. A method according to claim 4 including the step of masking the screw threads.

7. A method according to claim 6 including the step of applying a titanium nitride coating to the tool body whereby the titanium nitride coating is not applied to the screw threads.

8. The method according to claim 4 including the step of applying a titanium nitride coating to the tool body.

9. The method according to claim 8 wherein the step of applying includes preventing the titanium nitride coating from being applied to the screw threads.

10. A method according to claim 1, further including the step of locating the transition between the first and second bores at a node.

11. A method according to claim 1 wherein the step of machining includes forming the probe portion to define a circular cross-sectional dimension whereby the diameter of the probe portion gradually decreases from a proximal end of the probe portion to a distal end of the probe portion.

12. A method for manufacturing an aspirating tool for use with a surgical apparatus for ultrasonically fragmenting and aspirating tissue, comprising the steps of:

forming an elongated metal stock to define an ultrasonic tool body having an enlarged portion and an elongated probe portion extending distally from the enlarged portion, the probe portion having an outer diameter which gradually decreases from a proximal end of the probe portion to a distal end of the probe portion;

boring a first bore at least partially through the enlarged portion in coaxial arrangement with a longitudinal axis of the tool body, the first bore defining a first internal diameter; and boring a second bore at least partially through the elongated probe portion in coaxial arrangement with the longitudinal axis of the tool body and in communication with the first bore, the second bore defining a second internal diameter greater than the first internal diameter.

13. The method according to claim 12 including the step of applying a titanium nitride coating to the tool body.

14. The method according to claim 13 including the step of forming screw threads on the enlarged portion of the tool body.

15. The method according to claim 14 including the step of masking the screw threads whereby, during the step of applying, the titanium nitride coating is not applied to the screw threads.

* * * * *